US006611328B2

(12) United States Patent
Isozaki et al.

(10) Patent No.: US 6,611,328 B2
(45) Date of Patent: Aug. 26, 2003

(54) SURFACE INSPECTING APPARATUS AND METHOD

(75) Inventors: Hisashi Isozaki, Tokyo (JP); Yutaka Shida, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 198 days.

(21) Appl. No.: 09/785,541

(22) Filed: Feb. 20, 2001

(65) Prior Publication Data

US 2002/0021438 A1 Feb. 21, 2002

(30) Foreign Application Priority Data

Feb. 24, 2000 (JP) .................................. 2000-047920

(51) Int. Cl.[7] .................................................. G01N 21/00
(52) U.S. Cl. ................................................... 356/237.5
(58) Field of Search ........................... 356/237.1–237.5

(56) References Cited

U.S. PATENT DOCUMENTS

| 5,859,698 | A | * | 1/1999 | Chau et al. ............... 356/237.2 |
| 6,038,018 | A | * | 3/2000 | Yamazaki et al. ........ 356/237.1 |
| 6,104,481 | A | * | 8/2000 | Sekine et al. ............. 356/237.5 |
| 6,201,601 | B1 | * | 3/2001 | Vaez-Iravani et al. ... 356/237.4 |
| 6,271,916 | B1 | * | 8/2001 | Marxer et al. ............ 356/237.3 |
| 6,384,910 | B2 | * | 5/2002 | Vaez-Iravani et al. ... 356/237.2 |

\* cited by examiner

*Primary Examiner*—Michael P. Stafira
(74) *Attorney, Agent, or Firm*—Foley & Lardner

(57) ABSTRACT

The surface inspection apparatus comprises a light source section for emitting a first luminous flux and a second luminous flux; a first irradiation optical system in which the first luminous flux is irradiated on the surface of an inspected object at a first irradiation angle; a second irradiation optical system in which the second luminous flux is irradiated on the surface of an inspected object at a second irradiation angle different from the first irradiation angle; a displacement section for relatively displacing an inspected object and an irradiation luminous flux of the irradiation optical system; a light receiving optical system for receiving scattered light of the first luminous flux irradiated by the first irradiation optical system and produced from an inspection object on the surface of an inspected object and scattered light of the second luminous flux irradiated by the second irradiation optical system and produced from an inspection object on the surface of an inspected object; a first light receiving section for converting scattered light of the first luminous flux received by the light receiving optical system into a first light receiving signal; a second light receiving section for converting scattered light received by the light receiving optical system into a second light receiving signal; an inspection object distribution data forming section for forming inspection object distribution data on the basis of the first light receiving signal and the second light receiving signal; and a scratch processing section for scratch-processing inspection object distribution data.

6 Claims, 10 Drawing Sheets

(a)

(b)

(c)

SURFACE INSPECTING APPARATUS AND METHOD

FIELD OF THE INVENTION

The present invention relates to a surface inspection method and apparatus for detecting inspection objects (such as foreign matter and scratches) on the surface of a wafer and other inspected objects.

PRIOR ART

In the conventional surface inspection apparatus, foreign matter and scratches on the surface of an inspected object are measured by placing a luminous flux incident in the form of high incidence or low incidence. However, with the trend of higher sensitivity of the surface inspection apparatus and fineness of steps, in a bare wafer (Bare-Si), a portion where a sensitivity range of detection of foreign matter and a sensitivity range of detection of scratches are superposed is smaller, which poses a problem.

Therefore, in the high sensitivity detection for placing a luminous flux in low incidence, the surface information of an inspected object is conversely less to sometimes result in a phenomenon that scratches are not detected.

On the other hand, in the detection with sensitivity sensitive to the surface information, the scratches can be detected, but the detection sensitivity of foreign matter is deteriorated.

With the trend of higher sensitivity of the surface inspection apparatus and fineness of steps, particularly in a bare wafer, there has been desired that detection of scratches as the surface information and detection of smaller foreign matter on the surface of an inspected object can be carried out simultaneously.

In the conventional surface inspection apparatus, it has been impossible to detect foreign matter with high sensitivity, and detect scratches as the surface information with high sensitivity to separate and measure both the foreign matter and scratches with high accuracy.

SUMMARY OF THE INVENTION

An object of the present invention is to enable separation and detection of both foreign matter and scratches.

The present invention provides a surface inspection apparatus and method for detecting inspection objects (such as foreign matter and scratches) on the surface of a wafer and other inspected objects.

According to one mode of the present invention, there comprises a light source section for emitting a first luminous flux and a second luminous flux; a first irradiation optical system in which the first luminous flux is irradiated on the surface of an inspected object at a first irradiation angle; a second irradiation optical system in which the second luminous flux is irradiated on the surface of an inspected object at a second irradiation angle different from the first irradiation angle; a displacement section for relatively displacing an inspected object and an irradiation luminous flux of the irradiation optical system; a light receiving optical system for receiving scattered light of the first luminous flux irradiated by the first irradiation optical system and produced from an inspection object on the surface of an inspected object and scattered light of the second luminous flux irradiated by the second irradiation optical system and produced from an inspection object on the surface of an inspected object; a first light receiving section for converting scattered light of the first luminous flux received by the light receiving optical system into a first light receiving signal; a second light receiving section for converting scattered light of the second luminous flux received by the light receiving optical system into a second light receiving signal; a inspection object distribution data forming section for forming inspection object distribution data on the basis of the first light receiving signal and the second light receiving signal; and a scratch processing section for scratch-processing the inspection object distribution data.

Preferably, a first characteristic of the first luminous flux emitted by the light source section, and a second characteristic of the second luminous flux emitted by the light source section are a wavelength of luminous flux or a polarized light component. The first irradiation angle of the first irradiation optical system is set to be smaller than the second irradiation angle of the second irradiation optical system.

Preferably, the scratch processing section processes false scratches or genuine scratches of the inspection object in the inspection object distribution data as fictitious scratches to scratch-process the inspection object distribution data to form scratch distribution data. The scratch processing section removes data of the inspection object processed as the false scratches from that of the inspection object obtained from the first light receiving signal or the second light receiving signal to thereby form foreign matter distribution data.

BRIEF DESCRIPTION OF THE DRAWINGS

FIG. 8(a) shows one example of an inspection object to be inspected on the high incident side.

FIG. 8(b) shows one example of an inspection object to be inspected on the low incident side.

FIG. 8(c) shows inspection object distribution data.

FIG. 8(d) shows scratch processing of inspection object distribution data.

FIG. 8(e) shows foreign matter distribution data.

FIG. 8(f) shows scratch distribution data.

FIG. 9(a) is a schematic view of inspection object data on the high incident side shown in FIG. 8(a) to be object for scratch processing.

FIG. 9(b) is a schematic view of inspection object data on the low incident side shown in FIG. 8(b) to be object for scratch processing.

FIG. 9(c) is a schematic view of inspection object data for scratch processing in inspection object distribution data.

DESCRIPTION OF THE PREFERRED EMBODIMENTS

Figure 1:
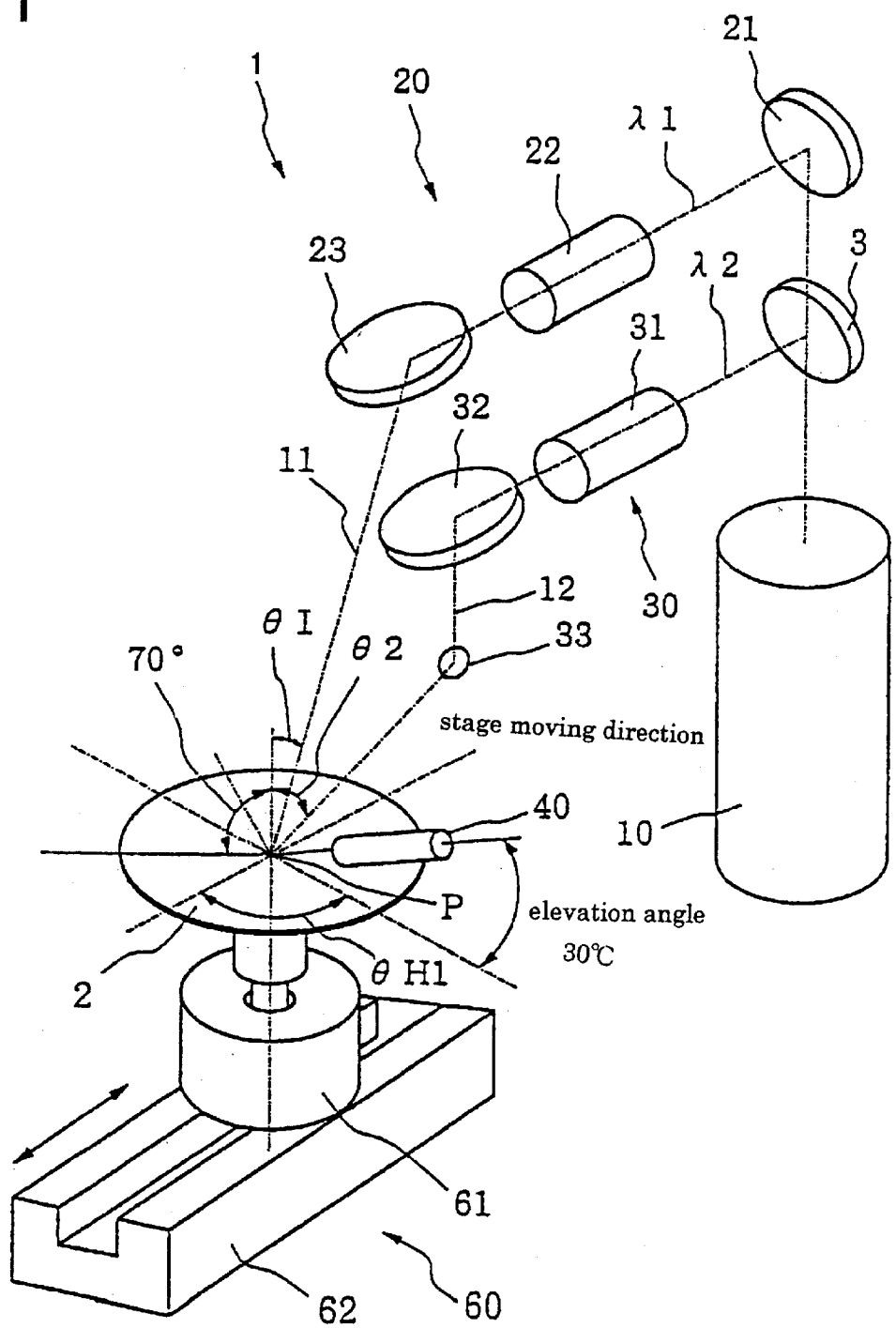
FIG. 1 is a schematic arrangement view of main optical elements of a surface inspection apparatus according to one preferred embodiment of the present invention.

FIG. 1 is a schematic arrangement view of main optical elements of a surface inspection apparatus according to preferred one embodiment of the present invention.

A surface inspection apparatus 1 comprises a light source section 10 such as a laser tube for emitting at least a luminous flux 11 of a first wavelength $\lambda 1$ and a luminous flux 12 of a second wavelength $\lambda 2$, a first irradiation optical system 20 for irradiating the luminous flux 11 of a first wavelength $\lambda 1$ from the light source section 10 on a semiconductor wafer 2 as an inspected object at a first irradiation angle $\theta 1$, a second irradiation optical system 30 for irradiating the luminous flux 12 of a second wavelength $\lambda 2$ from the light source section 10 on an inspection point P on the surface of the semiconductor wafer 2 at a second irradiation angle $\theta 2$, a first light receiving optical system 40 for receiving scattered light from the inspection point P on the surface of the semiconductor wafer 2 caused by the luminous fluxes 11, 12 irradiated by the first irradiation optical system 20 and the second irradiation optical system 30 in first scattering direction, and a displacement section 60 for allowing the semiconductor wafer 2 as an inspected object to enable straight and rotational movement relatively with respect to the luminous flux 11 of the first irradiation optical system 20. An angle of elevation of the first light receiving optical system 40 in FIG. 1 is 30°.

The light source section 10 will be explained. The light source section 10 emits at least the luminous flux 11 of a first wavelength, the second luminous flux 12 of a second wavelength different therefrom. As the light source section 10, various kinds of sources emitting fluxes of a plurality of wavelengths can be used. For example, employed are one that luminous fluxes of a plurality of wavelengths are emitted by a single light source, for example, such as a laser of multi-line, and the other that luminous fluxes of a plurality of light sources emitting fluxes of different wavelengths are combined by a half mirror or the like to form a single beam.

Where when a laser of mutiline is employed, luminous fluxes of unnecessary wavelength emit, the flux is caused to pass through a band pass filter passing through the first wavelength and the second wavelength to thereby enable extraction of only the luminous flux of necessary wavelength.

Where a plurality of light sources emitting luminous fluxes of different wavelengths is used, a plurality of luminous fluxes are combined by a half mirror or the like to form a single beam.

Where in an example of FIG. 1, an argon ion laser is used as the light source section 10, a wavelength of 488 nm and a wavelength of 514.5 nm can be selected. A luminous flux emitted from the light source section 10 causes the luminous flux 11 of a wavelength $\lambda 1$ to pass through, and a luminous flux emitted form the light source section 10 by a dichroic mirror 3 to reflect the luminous flux 12 of a second wavelength $\lambda 2$ causes the luminous flux 11 of a first wavelength and the luminous flux 12 of a second wavelength to be separated. The luminous flux 11 of a first wavelength is changed in direction by a first mirror 21, and is irradiated on an irradiation point P on the surface of an inspected object 2 at a first irradiation angle $\theta 1$ through a group of first irradiation lenses 22 and a second mirror 23. The luminous flux 12 of a second wavelength is reflected by a dichroic mirror 3, and is irradiated on an irradiation point P on the surface of an inspected object 2 at a second irradiation angle $\theta 2$ through a group of second irradiation lenses 31, a third mirror 32 and a fourth mirror 33.

Where an inspection object (that is, scratch, foreign matter, etc.) is present on the irradiation point P, when the irradiation luminous flux is irradiated thereon, scattered light occurs in accordance with a fixed directivity. The first irradiation angle $\theta 1$ and the second irradiation angle $\theta 2$ are set with a normal direction of the inspected object 2 as a reference. In the embodiment of FIG. 1, as the first irradiation angle $\theta 1$, a fixed angle is selected from the range of 0 to 40 degree as an incident angle. As the second irradiation angle $\theta 2$, a fixed angle is selected from the range of 50 to 85 degree as an incident angle. The horizontal direction maybe either the same or different.

In the embodiment of FIG. 1, there is established a relationship of the first irradiation angle $\theta 1$<the second irradiation angle $\theta 2$. The magnitude of the first wavelength $\lambda 1$ and the second wavelength $\lambda 2$ can be optionally selected. Since there is the tendency that the larger the incident angle, the detection sensitivity is enhanced, and the shorter the using wavelength $\lambda$, the detection sensitivity is enhanced, if the second wavelength $\lambda 2$ is shorter than the second wavelength $\lambda 1$ (the first wavelength $\lambda 1$>the second wavelength $\lambda 2$), it can be set in a direction that the detection sensitivity due to the first irradiation angle $\theta 1$ is equal to the detection sensitivity due to the second irradiation angle $\theta 2$.

Next, the first light receiving optical system 40 will be explained.

The first light receiving optical system 40 for receiving the aforementioned scattered light is provided. The first light receiving optical system 40 receives, from a first light receiving direction, the scattered light form the inspection point P on the surface of the semiconductor wafer 2 caused by the luminous fluxes 11, 12 irradiated by the first irradiation optical system 20 and the second irradiation optical system 30.

A first light receiving horizontal angle $\theta H1$ (for example, 90°) in a first light receiving direction is measured, as a reference, a reflecting direction when the irradiation luminous fluxes 11, 12 caused by the first irradiation optical system 20 or the second irradiation optical system 30 is mirror-reflected by the inspected object 2. The light receiving elevation angle in the first light receiving direction is set, for example, to 30°.

Figure 2:
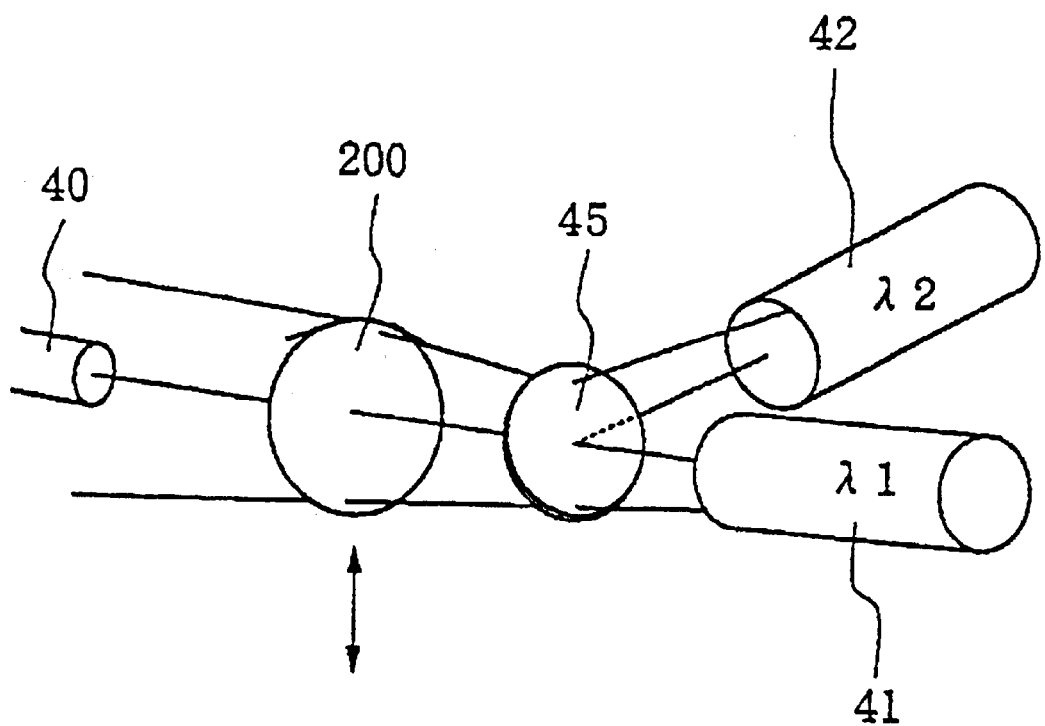
FIG. 2 is a detailed view of a light receiving optical system of the surface inspection apparatus according to one preferred embodiment of the present invention.

As shown in FIG. 2, the receiving luminous flux received by the first light receiving optical system 40 is separated by a second dichroic mirror 45 into the luminous flux of a first wavelength $\lambda 1$ and the luminous flux of a second wavelength $\lambda 2$ via an ND filter 200 arranged movably in a direction of arrow so that the luminous flux is inserted into or moved away from a light receiving optical path. The first light receiving section 41 receives the scattered light of a first wavelength $\lambda 1$ received by the first light receiving optical system 40 to convert it into a first light receiving signal. The second light receiving section 42 receives the scattered light of a second wavelength λ2 received by the first light receiving optical system 40 to convert it into a second light receiving signal. The first light receiving section 41 and the second light receiving section 42 is desired to be a light receiving element such as a photomultiplier.

The displacement section 60 will now be described. The displacement section 60 comprises a rotation displacement section 61 for rotating and displacing an inspected object 2, and a straight-line displacement section 62 for straight-line displacing an inspected object 2. The straight-line displacement is merely moved at the fixed rate of the width of luminous flux with respect to displacement of one rotation of the rotation displacement section 61 to spirally scan the inspected object 2 throughout by irradiation light of the first and second irradiation optical systems 20, 30.

The present invention is not limited to the scanning method as described above, but the irradiation luminous flux may be subjected to straight-line scanning by a polygon mirror or the like in place of the rotation displacement.

In the embodiment of FIG. 1, the rotation displacement section 61 comprises a rotation motor for rotating a rotation table. The straight-line displacement section 62 comprises a slide movement section for moving the rotation motor linearly. The slide movement section causes, by movement thereof, an irradiation position of the irradiation luminous fluxes 11, 12 of the irradiation optical systems 20, 30 to be displaced so as to pass through the center of the inspected object 2 to cross in a diametrical direction.

Figure 3:
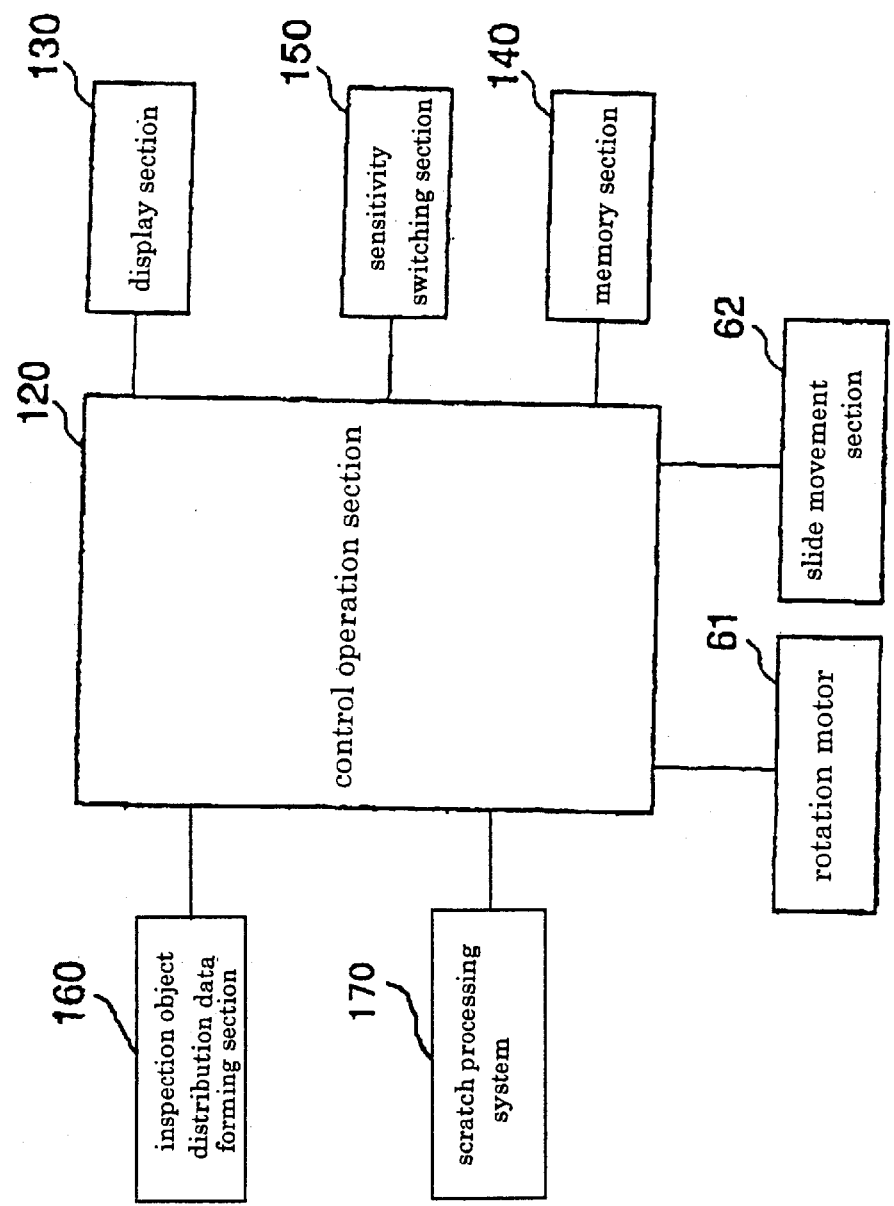
FIG. 3 is a block diagram of the surface inspection apparatus shown in FIG. 1.

FIG. 3 is a block diagram of the surface inspection apparatus shown in FIG. 1. A control operation section 120 carries out fixed signal processing described later to display the inspection result or the processing result on a display section 130 as necessary, to store it in a memory section 140, or to read the stored content. The control operation section 120 forms inspection object distribution data described later in a inspection object distribution data forming section. Further, the control operation section 120 applies scratch processing described later to the aforementioned inspection object distribution data in a scratch processing section 170. Further, the control operation section 120 controls a rotational motor of the rotation displacement section 61 or the slide movement section of the straight-line displacement section 62, and controls a sensitivity switching section 150 of the first light receiving section 41 and the second light receiving section 42.

The sensitivity switching section 150 moves the ND filter 200 in a direction of arrow in FIG. 2 to insert the ND filter 200 into a light receiving window of the first light receiving section 41 and the second light receiving section 42 to lower the sensitivity or to separate the ND filter 200 from the light receiving window to raise the sensitivity, thereby carrying out switching of sensitivity.

When the first light receiving section 41 and the second light receiving section 42 are formed from a photomultiplier, the sensitivity can be switched by regulation of voltage applied thereto.

Next, extraction processing of inspection object data from the first light receiving signal and the second light receiving signal will be described.

Figure 4:
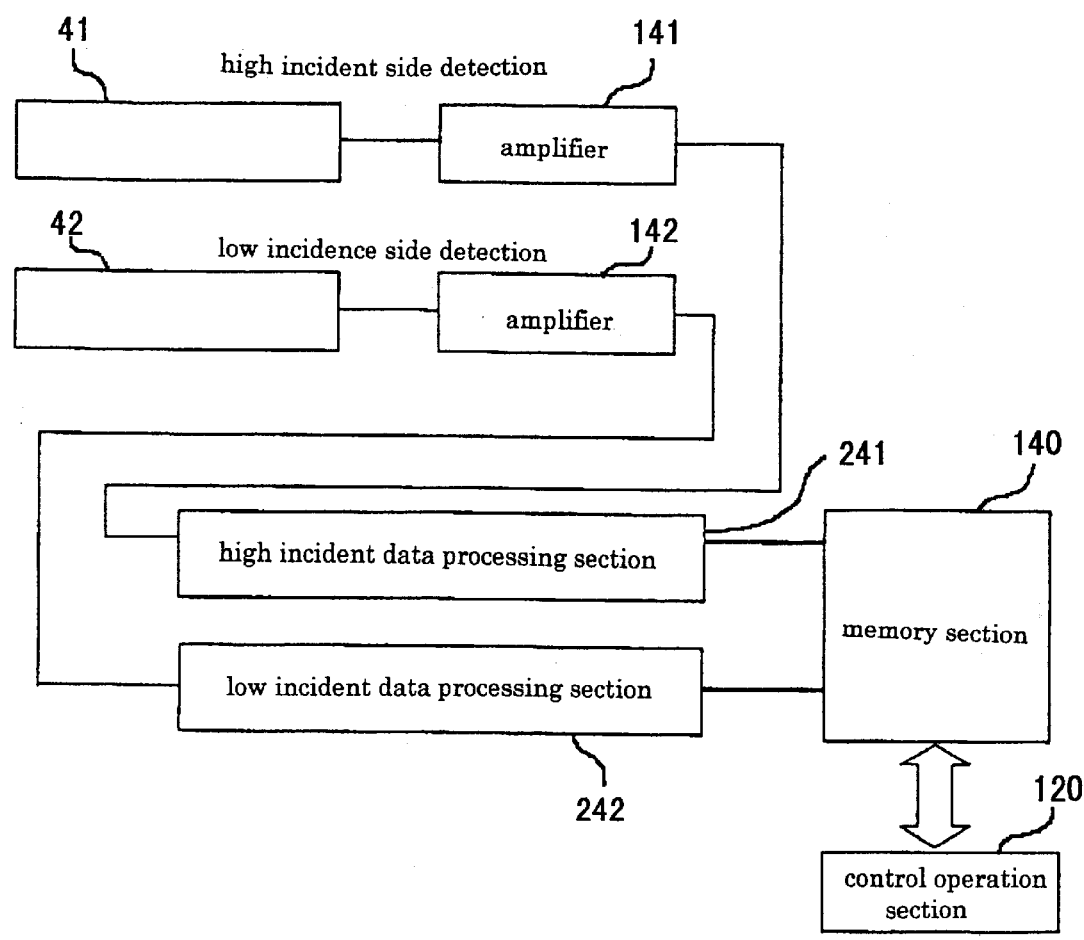
FIG. 4 is a system block diagram of inspection object data extraction processing of the surface inspection apparatus according to one preferred embodiment of the present invention.

FIG. 4 is a system block diagram of the extraction processing of inspection object data.

In FIG. 4, the scattered light of the first luminous flux 11 (FIG. 1) received by the light receiving optical system 40 is converted into the first light receiving signal by the first light receiving section 41. The scattered light of the second luminous flux 12 (FIG. 1) received by the light receiving optical system 40 is converted into the second light receiving signal by the second light receiving section 42. The first light receiving signal is sent to a high incident data processing section 241 through an amplifier 141. The first light receiving signal is subjected to fixed data processing in the high incident data processing section 241. The first light receiving signal subjected to the fixed data processing is stored in the memory section 140. The second light receiving signal is sent to a low incident data processing section 242 through an amplifier 142. The second light receiving signal is subjected to fixed data processing in the low incident data processing section 242. The second light receiving signal subjected to the fixed data processing is stored in the memory section 140. The first light receiving signal subjected to the fixed data processing and stored in the memory section 140 is subjected to the inspection object data extraction processing by the control operation section 120. The extracted inspection object data is stored in the memory section 140. The second light receiving signal subjected to the fixed data processing and stored in the memory section 140 is subjected to the inspection object data extraction processing by the control operation section 120. The extracted inspection object data is stored in the memory section 140.

Figure 5:
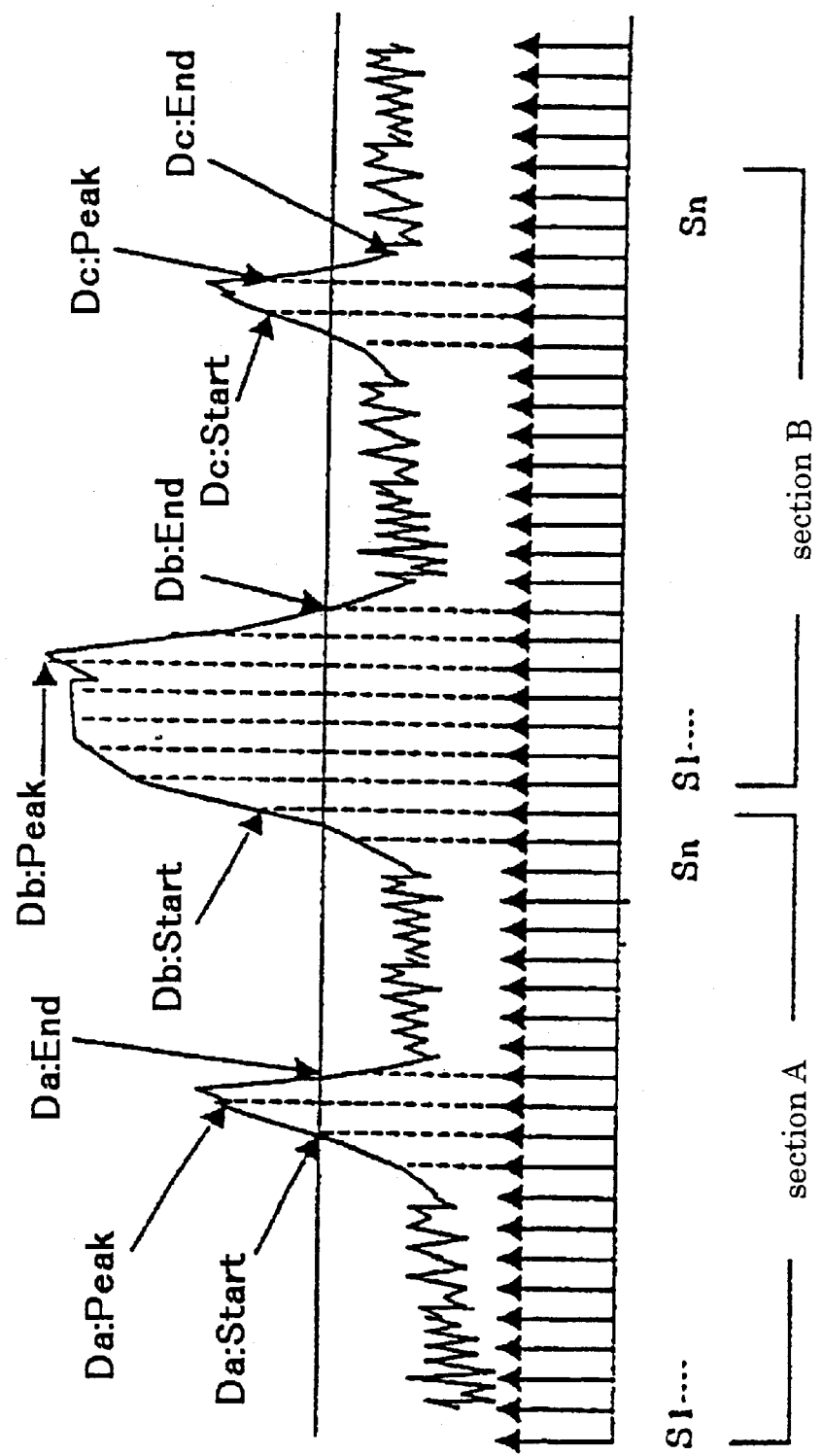
FIG. 5 is a view showing the construction of inspection object data in a light receiving signal of the surface inspection apparatus according to preferred one embodiment of the present invention.
Figure 6:
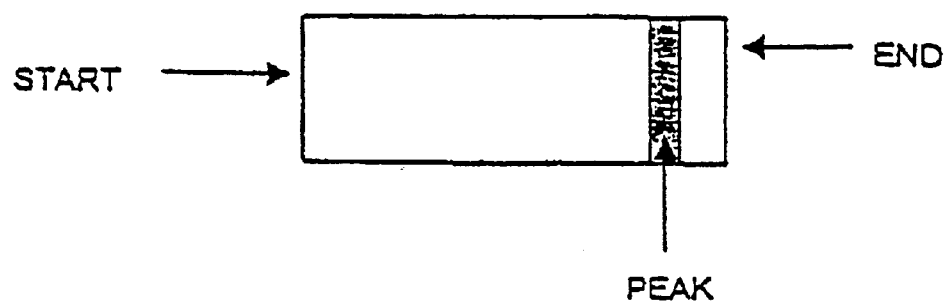
FIG. 6 is a schematic view showing the inspection object data of the surface inspection apparatus according to preferred one embodiment of the present invention.

FIG. 5 is a view showing one example of the construction of inspection object data in the light receiving signal. FIG. 6 is a schematic view showing one example of inspection object data.

When detection light is scanned in a fixed direction and when scattered signal of an inspection object exceeds a threshold signal (shown by the solid line horizontally in FIG. 5), that is stored as a start coordinate (Start); thereafter, when the scattered signal of an inspection object lowers than the threshold signal, that is stored as an end coordinate (End); and that the scattered signal of an inspection object is greatest between the Start coordinate and the End coordinate is stored as a peak level value (Peak). An inspection object on the surface of an inspected object is specified on the basis of inspection object data comprising the start coordinate (Start), the peak level value (Peak) and the end coordinate (End).

In FIG. 5, since Da, Db and Dc are specified, the number of inspection objects is three. In this case, data between sections A and B has nothing to do with the number of inspection objects, and three is counted as the number of inspection objects.

Figure 7:
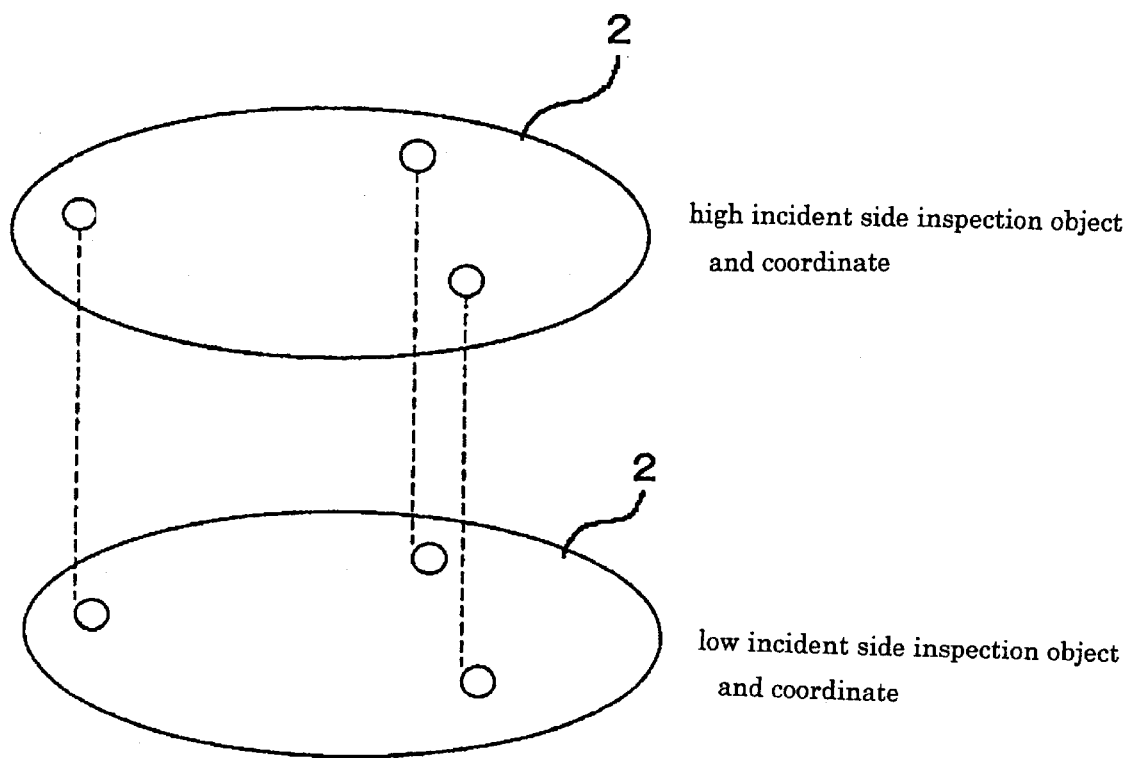
FIG. 7 is an explanatory view of a coordinate alignment of the surface inspection apparatus according to a preferred embodiment of the present invention.

FIG. 7 is an explanatory view of a coordinate alignment. Such a coordinate alignment is carried out in the following manner.

The coordinates of an inspection object detected on the high incident side is obtained from the inspection object data obtained from the first light receiving signal. Further, the coordinates of an inspection object detected on the low incident side is obtained from the inspection object data obtained from the second light receiving signal. The coordinate alignment (coordinate adjustment) is carried out using several coordinates of the inspection object detected on the high incident side and the inspection object detected on the low incident side. The coordinates on the high incident side are adjusted to the coordinates on the low incident side by carrying out the coordinate alignment (coordinate adjustment).

Next, the formation of inspection object distribution data will be explained.

Figure 8:
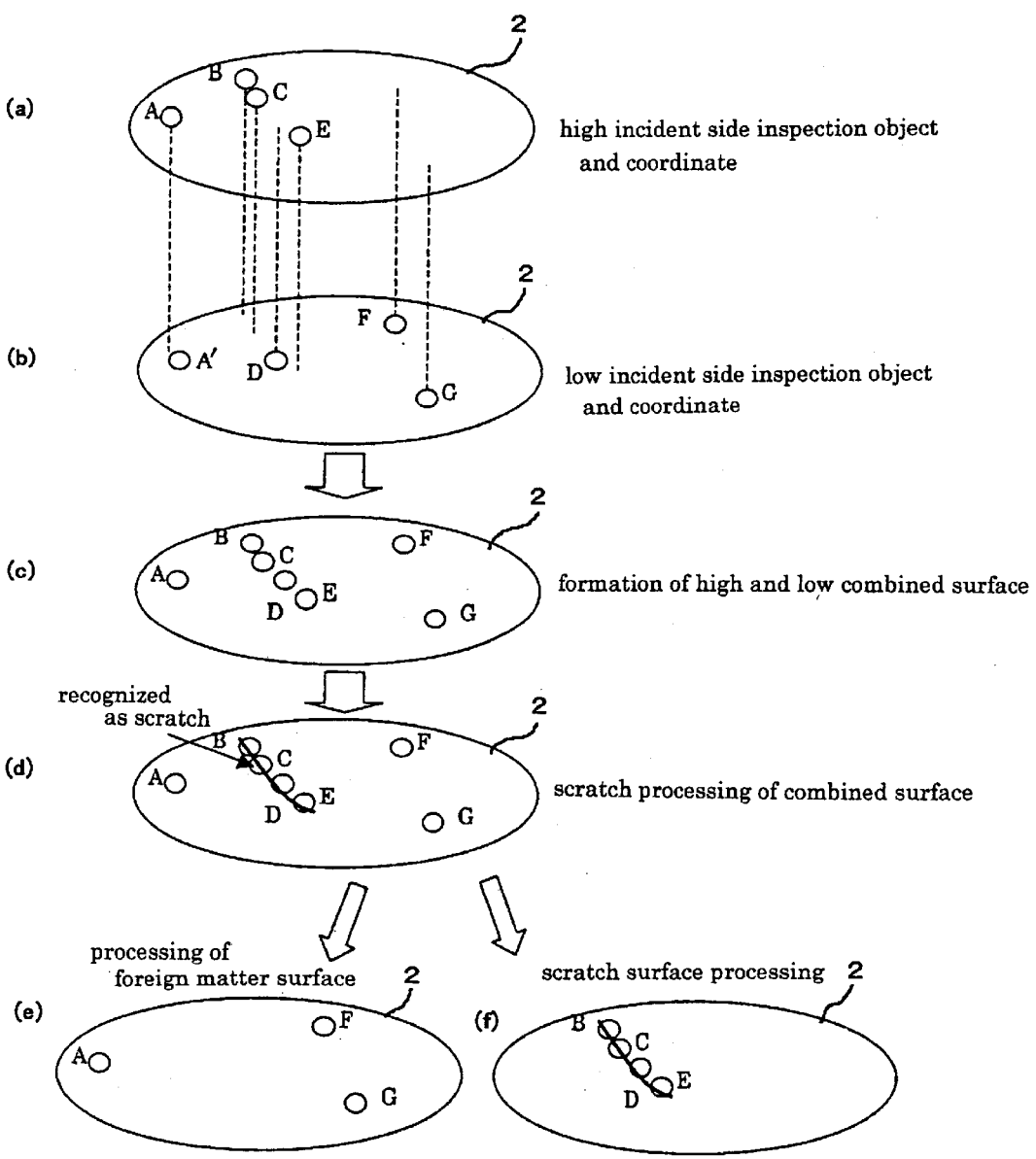
FIG. 8 is a view showing various images.

For example, inspection objects A, B, C, E are detected on the inspected object 2 by detection on the high incident side, as shown in FIG. 8(a). For example, inspection objects A', D, F, G are detected on the inspected object 2 by detection on the low incident side, as shown in FIG. 8(b). The high incident side is high sensitivity with respect to detection of scratches, but is low sensitivity with respect to detection of foreign matter. The low incident side is high sensitivity with respect to detection of foreign matter, but is low sensitivity with respect to detection of scratches.

The coordinates of the inspection objects A, B, C, E and inspection objects A', D, F, G are obtained by a inspection object distribution data forming section 160, and the coordinate alignment is carried out as described above.

FIG. 8(c) is an image view of inspection object distribution data. Inspection object distribution data (combined surface) having information of positions of inspection objects on an inspected object 2 are formed, as shown in FIG. 8(c), on the basis of the coordinates of the inspection objects A, B, C, E and inspection objects A', D, F, G, by the inspection object distribution data forming section 160 after the coordinate alignment.

Next, the scratch processing of inspection object distribution data will be explained.

Figure 9:
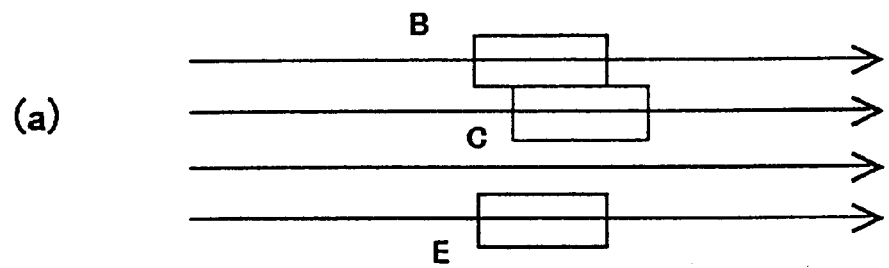
FIG. 9 is a schematic view of various inspection object data.
Figure 9:
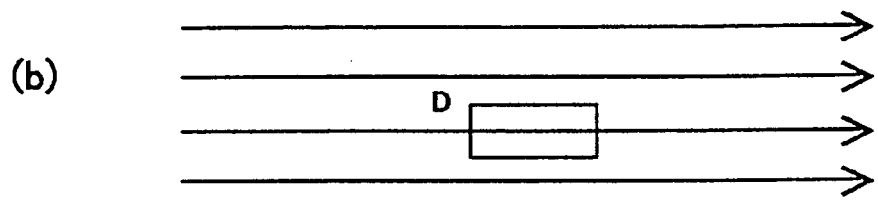
Figure 9:
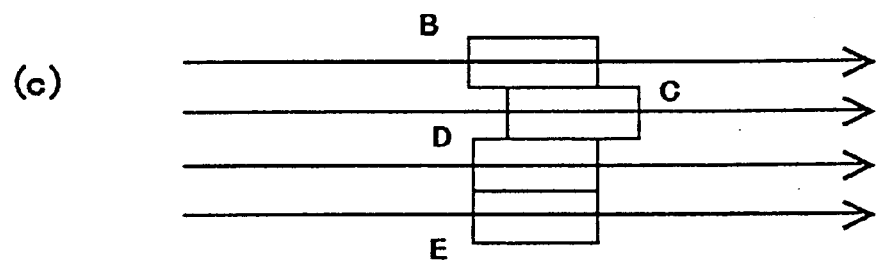

FIG. 8(d) is an image view of the scratch processing of inspection object distribution data. FIG. 9(a) is a schematic view of inspection object data on the high incident side shown in FIG. 8(a), which is an object for the scratch processing. FIG. 9(b) is a schematic view of inspection object data on the low incident side shown in FIG. 8(b), which is an object for the scratch processing. FIG. 9(c) is a schematic view of inspection object data which is an object for the scratch processing in the inspection object distribution data.

The inspection object data included in the inspection object distribution data is not distinguished whether it is data of an inspection object detected on the high incident side or data of an inspection object detected on the low incident side, but is handled as data on the same plane. And, inspection object distribution data are formed from the inspection object data detected on the high incident side and the inspection object data detected on the low incident side. Further, the inspection object included in the inspection object distribution data is not distinguished whether it is an inspection object detected on the high incident side or an inspection object detected on the low incident side, but as data on one plane, the inspection object distribution data is scratch-processed by the scratch processing section 170.

The scratch processing section carries out the scratch processing on the basis of the inspection object data included in the inspection object distribution data, the quantity of scattered light from the inspection object, and the continuity of the inspection object in the inspection object distribution data. Where a convex inspection object (false scratch) less than a fixed height and a concave inspection object (genuine scratch) are continuously detected in the inspection object distribution data, the scratch processing section 170 processes these inspection objects as fictitious scratches as a whole. Where only the concave inspection object is continuously detected in the inspection object distribution data, the scratch processing section processes these inspection objects as genuine scratches.

The scratch processing section 170 forms scratch distribution data, as shown in FIG. 8(f), on the basis of the data of inspection object having the false scratch or the genuine scratch processed as the fictritious scratch. The scratch distribution data are stored in the memory section 140.

The data of inspection object having the false scratch or the genuine scratch processed as the fictitious scratch is deleted from the data of inspection object obtained on the low incident side (side which is high in sensitivity with respect to detection of foreign matter) by the scratch processing section 170. In the data of inspection object obtained on the low incident side, the data of inspection object having the false scratch or the genuine scratch processed as the fictitious scratch is deleted to form foreign matter distribution data as shown in FIG. 8(e). The foreign matter distribution data is stored in the memory section 140.

In the scratch distribution data and the foreign matter distribution data stored in the memory section 140, the number and position of fictitious scratch (genuine scratch, false scratch), and the number and position of foreign matter are respectively distinguished and displayed on the display section 130.

In the manner as described above, the foreign matter and fictitious scratch (genuine scratch, false scratch) can be separated and detected with accuracy.

The present invention is not limited to the above-described embodiments.

Figure 10:
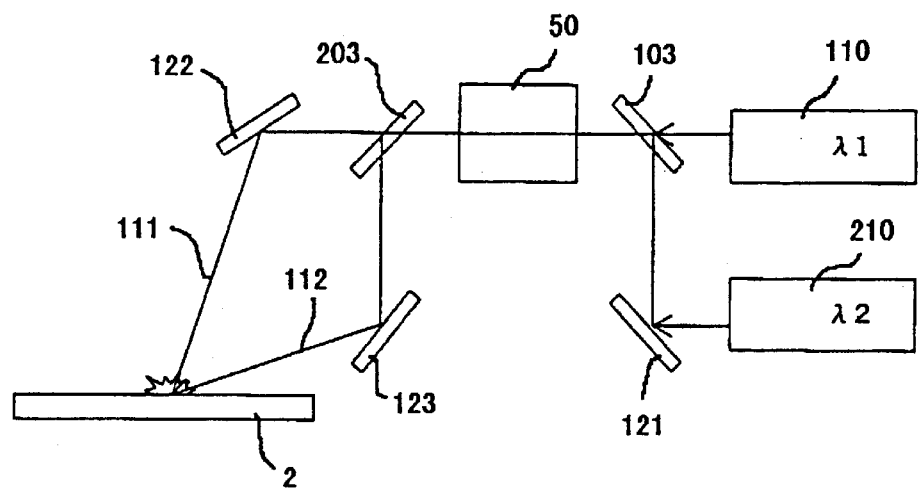
FIG. 10 is a block diagram of a system having a plurality of light sources emitting luminous fluxes of different wavelengths.
Figure 11:
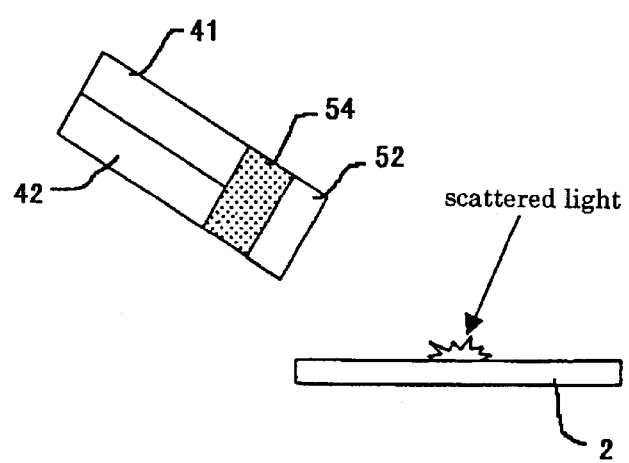
FIG. 11 is a block diagram of a detection system used in the system shown in FIG. 10.

As the light source section 10 shown in FIG. 1, a plurality of light sources 110, 210 emitting luminous fluxes of different wavelengths may be used as shown in FIG. 10.

In this case, the light sources 110, 210 can be controlled in ON/OFF. A luminous flux 111 emitted from the light source 110 passes through a half mirror 103. A luminous flux 112 emitted from the light source 210 is reflected by a mirror 121. The luminous flux 112 reflected by the mirror 121 is reflected by the half mirror 103. The luminous flux 111 and the luminous flux 112 pass through a lens unit 50. The lens unit has beam shaping function and polarized light selecting function.

The luminous flux 111 having passed through the lens unit 50 passes through a dichroic mirror 203 having wavelength discriminating function and is reflected by the mirror 122 and irradiated on the inspected object 2. The luminous flux 112 having passed through the lens unit 50 passes through the dichroic mirror 203 and is reflected by the mirror 123 and irradiated on the inspected object 2. The scattered light generated as the luminous fluxes 111, 112 are irradiated on the inspected object 2 is detected by a detection system comprising a lens 52, a wavelength discriminating element 54 and light receiving elements 41, 42.

In the manner as described above, the foreign matter and fictitious scratch (genuine scratch, false scratch) can be separated and detected with accuracy, similarly to that mentioned above.

The following becomes enabled by this invention.

Using the surface inspection apparatus comprising a projection system for causing luminous fluxes different in wavelength from each other to be incident on inspected objects at incident angles different from each other and a detection system having light receiving sections different from each other for each wavelength, fictitious scratch and foreign matter can be separated and measured more definitely.

Detection of high sensitivity with respect to foreign matter and detection of high sensitivity with respect to fictitious scratch are carried out to combine these detection results for processing, whereby fictitious scratch and foreign matter can be separated and measured with accuracy.

What is claimed is:

1. A surface inspection apparatus comprising:
    a light source section for emitting a first luminous flux and a second luminous flux irradiated on the surface of an inspected object;

a first irradiation optical system in which the first luminous flux is irradiated on the surface of an inspected object at a first irradiation angle;

a second irradiation optical system in which the second luminous flux is irradiated on the surface of an inspected object at a second irradiation angle different from the first irradiation angle;

a displacement section for relatively displacing an inspected object and an irradiation luminous flux of the irradiation optical system;

a light receiving optical system for receiving scattered light of the first luminous flux irradiated by the first irradiation optical system and produced from an inspection object on the surface of an inspected object and scattered light of the second luminous flux irradiated by the second irradiation optical system and produced from an inspection object on the surface of an inspected object;

a first light receiving section for converting scattered light of the first luminous flux received by the light receiving optical system into a first light receiving signal;

a second light receiving section for converting scattered light of the second luminous flux received by the light receiving optical system into a second light receiving signal;

an inspection object distribution data forming section for forming inspection object distribution data on the basis of the first light receiving signal and the second light receiving signal; and a scratch processing section for scratch-processing inspection object distribution data, wherein the scratch processing section processes a false scratch or a genuine scratch of an inspection object as fictitious scratch whereby inspection object distribution data is subjected to scratch processing to form scratch distribution data.

2. A surface inspection apparatus comprising:

a light source section for emitting a first luminous flux and a second luminous flux irradiated on the surface of an inspected object;

a first irradiation optical system in which the first luminous flux is irradiated on the surface of an inspected object at a first irradiation angle;

a second irradiation optical system in which the second luminous flux is irradiated on the surface of an inspected object at a second irradiation angle different from the first irradiation angle;

a displacement section for relatively displacing an inspected object and an irradiation luminous flux of the irradiation optical system;

a light receiving optical system for receiving scattered light of the first luminous flux irradiated by the first irradiation optical system and produced from an inspection object on the surface of an inspected object and scattered light of the second luminous flux irradiated by the second irradiation optical system and produced from an inspection object on the surface of an inspected object;

a first light receiving section for converting scattered light of the first luminous flux received by the light receiving optical system into a first light receiving signal;

a second light receiving section for converting scattered light of the second luminous flux received by the light receiving optical system into a second light receiving signal;

an inspection object distribution data forming section for forming inspection object distribution data on the basis of the first light receiving signal and the second light receiving signal; and a scratch processing section for scratch-processing inspection object distribution data, wherein the scratch processing section removes data of inspection object processed as fictitious scratch from data of inspection object obtained from the first light receiving signal or the second light receiving signal to thereby form foreign matter distribution data.

3. A surface inspection apparatus comprising:

a light emitting means for emitting a first luminous flux and a second luminous flux irradiated on the surface of an inspected object;

a first irradiation means in which the first luminous flux is irradiated on the surface of an inspected object at a first irradiation angle;

a second irradiation means in which the second luminous flux is irradiated on the surface of an inspected object at a second irradiation angle different from the first irradiation angle;

a displacement means for relatively displacing an inspected object and an irradiation luminous flux;

a light receiving means for receiving scattered light of the first luminous flux irradiated by the first irradiation means and produced from an inspection object on the surface of an inspected object and scattered light of the second luminous flux irradiated by the second irradiation means and produced from an inspection object on the surface of an inspected object;

a first conversion means for converting scattered light of the first luminous flux received by the light receiving means into a first light receiving signal;

a second conversion means for converting scattered light of the second luminous flux received by the light receiving means into a second light receiving signal;

a data forming means for forming inspection object distribution data on the basis of the first light receiving signal and the second light receiving signal; and a scratch processing means for scratch-processing inspection object distribution data, wherein the scratch processing means processes a false scratch or a genuine scratch of an inspection object as fictitious scratch whereby inspection object distribution data is subjected to scratch processing to form scratch distribution data.

4. A surface inspection apparatus comprising:

a light emitting means for emitting a first luminous flux and a second luminous flux irradiated on the surface of an inspected object;

a first irradiation means in which the first luminous flux is irradiated on the surface of an inspected object at a first irradiation angle;

a second irradiation means in which the second luminous flux is irradiated on the surface of an inspected object at a second irradiation angle different from the first irradiation angle;

a displacement means for relatively displacing an inspected object and an irradiation luminous flux;

a light receiving means for receiving scattered light of the first luminous flux irradiated by the first irradiation means and produced from an inspection object on the surface of an inspected object and scattered light of the second luminous flux irradiated by the second irradiation means and produced from an inspection object on the surface of an inspected object;

a first conversion means for converting scattered light of the first luminous flux received by the light receiving means into a first light receiving signal;

a second conversion means for converting scattered light of the second luminous flux received by the light receiving means into a second light receiving signal;

a data forming means for forming inspection object distribution data on the basis of the first light receiving signal and the second light receiving signal; and a scratch processing means for scratch-processing inspection object distribution data, wherein the scratch processing means removes data of inspection object processed as fictitious scratch from data of inspection object obtained from the first light receiving signal or the second light receiving signal to thereby form foreign matter distribution data.

5. A surface inspection method comprising:

a step of emitting a first luminous flux and a second luminous flux irradiated on the surface of an inspected object;

a step of irradiating the first luminous flux on the surface of an inspected object at a first irradiation angle;

a step of irradiating the second luminous flux on the surface of an inspected object at a second irradiation angle different from the first irradiation angle;

a step of relatively displacing an inspected object and an irradiation luminous flux;

a step of receiving scattered light of the first luminous flux produced from an inspection object on the surface of an inspected object, and scattered light of the second luminous flux irradiated by the second irradiation optical system and produced from an inspection object on the surface of an inspected object;

a step of converting scattered light of the first luminous flux into a first light receiving signal;

a step of converting scattered light of the second luminous flux into a second light receiving signal;

a step of forming inspection object distribution data on the basis of the first light receiving signal and the second light receiving signal; and a step of scratch-processing inspection object distribution data, wherein the scratch processing step processes a false scratch or a genuine scratch of an inspection object as fictitious scratch whereby inspection object distribution data is subjected to scratch processing to form scratch distribution data.

6. A surface inspection method comprising:

a step of emitting a first luminous flux and a second luminous flux irradiated on the surface of an inspected object;

a step of irradiating the first luminous flux on the surface of an inspected object at a first irradiation angle;

a step of irradiating the second luminous flux on the surface of an inspected object at a second irradiation angle different from the first irradiation angle;

a step of relatively displacing an inspected object and an irradiation luminous flux;

a step of receiving scattered light of the first luminous flux produced from an inspection object on the surface of an inspected object, and scattered light of the second luminous flux irradiated by the second irradiation optical system and produced from an inspection object on the surface of an inspected object;

a step of converting scattered light of the first luminous flux into a first light receiving signal;

a step of converting scattered light of the second luminous flux into a second light receiving signal;

a step of forming inspection object distribution data on the basis of the first light receiving signal and the second light receiving signal; and a step of scratch-processing inspection object distribution data, wherein the scratch processing step removes data of inspection object processed as fictitious scratch from data of inspection object obtained from the first light receiving signal or the second light receiving signal to thereby from foreign matter distribution date.

* * * * *